United States Patent [19]
Lynn et al.

[11] Patent Number: 5,562,639
[45] Date of Patent: Oct. 8, 1996

[54] VENTED FLUID COLLECTION SYSTEM

[76] Inventors: Lawrence A. Lynn, 1275 Olentangy River Rd., Ste. 223, Columbus, Ohio 43212; Robert B. Guthrie, c/o Viggo-Spectramed, 1900 Williams Dr., Oxnard, Calif. 93030-2691

[21] Appl. No.: 155,863

[22] Filed: Nov. 23, 1993

Related U.S. Application Data

[60] Continuation-in-part of Ser. No. 935,907, Aug. 27, 1992, Pat. No. 5,466,219, which is a division of Ser. No. 594,677, Oct. 10, 1990, Pat. No. 5,178,607, which is a continuation of Ser. No. 302,835, Jan. 27, 1989, abandoned, which is a continuation-in-part of Ser. No. 80,406, Jul. 31, 1987, Pat. No. 4,838,855.

[51] Int. Cl.$^6$ .................................................. A61M 31/00
[52] U.S. Cl. ............................................................ 604/280
[58] Field of Search ............................... 604/4, 35, 280, 604/36, 38, 83, 86, 87, 88, 91, 117, 122, 201, 239, 244, 256, 905; 128/673, 760, 762–766

[56] References Cited

U.S. PATENT DOCUMENTS

| | | |
|---|---|---|
| 4,496,350 | 1/1985 | Consentino . |
| 4,666,438 | 5/1987 | Raulerson . |
| 4,721,506 | 6/1988 | Tenes . |
| 4,763,648 | 8/1988 | Wyatt . |
| 4,834,152 | 5/1989 | Howson et al. . |

*Primary Examiner*—John D. Yasko
*Assistant Examiner*—Manuel Mendez
*Attorney, Agent, or Firm*—Cushman Darby & Cushman, LLP

[57] ABSTRACT

A vented fluid collection system including a collection apparatus for use with a device in communication with a mammalian organ or body lumen having a fluid to be sampled therein. The fluid collection apparatus has a blunt cannula having a bore defined therein and a wall defining a small collection chamber in communication with the bore. A fluid sample passes through the bore and is stored in the collection chamber. A vented membrane is disposed at an opening in the wall to allow gas to pass therethrough but prevents fluid collected in the collection chamber from passing therethrough. A shroud surrounds and protects the cannula and a cannula cap may be mounted to the shroud to enclose the cannula. In an alternative design of the fluid collection apparatus, the bore acts as the collection chamber. In all designs, when the fluid collection system communicates with a blood vessel, the patient's systemic blood pressure urges the fluid sample into the bore and, in the first design, further into the collection chamber.

19 Claims, 5 Drawing Sheets

VENTED FLUID COLLECTION SYSTEM

This application is a Continuation-In-Part of U.S. application Ser. No. 07/935,907 filed on Aug. 27, 1992 now U.S. Pat. No. 5,466,219, which is a Divisional of U.S. application Ser. No. 07/594,677, filed Oct. 10, 1990 and issued as U.S. Pat. No. 5,178,607, which was a Continuation of U.S. application Ser. No. 07/302,835, filed Jan. 27, 1989, now abandoned, which was a Continuation-In-Part of U.S. application Ser. No. 07/080,406, filed Jul. 31, 1987 and issued as U.S. Pat. No. 4,838,855.

BACKGROUND AND SUMMARY OF THE INVENTION

This invention relates to a vented fluid collection system having a blunt cannula and small collection chamber for use with an aspirator assembly.

It is often necessary to draw blood or fluid from a patient for diagnostic purposes. In fact, many times it is necessary to draw several samples of the blood from a patient within a relatively short span of time to monitor bodily functions and/or to monitor drug therapies. However, repetitive blood sampling may significantly reduce the patient's blood supply which may result in the patient becoming anemic and thus require a blood transfusion to replenish the his/her blood supply. Blood transfusion exposes the patient to the risk of exposure to hepatitis or HIV.

Laboratory blood analysis systems in existence today are capable of performing accurate diagnostic tests on blood samples of less than 1 ml in volume. However, typically, samples many times greater than that required are drawn from the patient. Therefore, a need exists for a reliable blood collection system having a small blood collection chamber capable of drawing a small sample of blood thereby decreasing the rate of a patient's blood depletion when numerous blood samples are drawn and yet capable of drawing a sufficient quantity for the testing required. Furthermore, unlike conventional needle syringes, it would be desirable to provide a blood collection system defining a small fixed volume so that a nurse or phlebotomist can not accidentally draw an excessive and unnecessarily large amount of blood.

Another problem that exists with conventional blood sampling techniques is that a standard syringe having a sharp needle is typically used. The sharp needle of the syringe is inserted either into a patient or an aspirator assembly that communicates with the patient's vascular system. However, on occasion, a nurse or a phlebotomist drawing the blood sample may stick him or herself with the sharp needle and thus expose him or herself to the patient's illness(es) or vice versa. Therefore, it would also be desirable for the blood collection system to have a blunt needle that can be inserted into an aspirator assembly during blood sampling. Blunt needles such as those described in my earlier U.S. application Ser. No. 07/935,907 can be employed in the blood collection system of this invention. Also, aspirator assemblies such as those disclosed in my earlier U.S. application Ser. No. 07/935,907 can be employed to cooperate with the blunt needle when blood is being drawn, to enable the blunt needle to communicate with the patient's vascular system.

Thus, it is an object of the present invention to provide a vented blood collection system comprising a blood collection device having a blunt tipped cannula coupled to a small fixed volume collection chamber.

In a first design of the blood collection device, the blunt tipped cannula is coupled to an adjoining small fixed volume collection chamber. To take a blood sample, the blunt cannula is inserted into an aspirator assembly which is in communication with the patient's vascular system. The patient's systemic blood pressure causes blood from the patient's vascular system to flow through the aspirator into a bore in the blunt cannula and further into the small collection chamber. Although no external pumping force is needed to siphon the blood from the patient's vascular system, such force may be applied if desired, for example, if the patient has particularly low blood pressure.

The end of the small collection chamber opposite to the cannula has an opening therein. A membrane is disposed in the opening in the collection chamber to allow air present in the small collection chamber to escape as blood enters the collection chamber through the cannula. However, this membrane does not permit the blood collected in the collection chamber to escape.

Alternatively, the opening can be covered by a removable cap which has a vented membrane incorporated therein. The cap can advantageously be removed to expose the end of the collection chamber and instruments can then be attached to the end of the collection chamber as necessary.

The blood collection device further comprises a cannula shroud which longitudinally surrounds the blunt cannula. Preferably, cannula cap is removably attached to the cannula shroud to cover the blunt cannula and thereby maintain a sterile environment therefor before the blood collection device is used, to protect the tip from unintentional contact, and to further prevent the blood sample in the collection chamber from exiting the collection chamber through the bore during subsequent transport to the lab.

In a second design of the blood collection device, a bore in the blunt tipped cannula acts as the small fixed volume collection chamber. The bore extends longitudinally through the blunt cannula from the distal blunt end to the opposite, proximal end.

As in the first design, the patient's systemic blood pressure causes blood from the patient's vascular system to flow through the aspirator into the bore in the blunt cannula. Depending on the dimensions of the bore, capillary flow plays a role in the collection of the blood sample. No external pumping force is needed to siphon the blood from the patient's vascular system, but such force may be applied if desired.

Desirably, a membrane as in the first design is disposed at the proximal end of the cannula bore to allow air present in the bore to escape as blood enters the bore as described above. This membrane does not permit the blood collected in the bore to escape.

The second design of the blood collection device may further comprise an enlarged housing longitudinally surrounding the blunt cannula to facilitate handling thereof. The enlarged housing may be injection molded about the blunt cannula or have an opening longitudinally therein into which the blunt cannula can be removably inserted.

The second design may be further modified to comprise a cannula shroud longitudinally surrounding the blunt cannula. The cannula shroud may be integral with the cannula or extend from an enlarged housing as described above. A cannula cap may be removably attached to the cannula and/or cannula shroud to cover the blunt cannula and thereby maintain a sterile environment therefor before the blood collection device is used, to protect the cannula tip from unintentional contact, and to further prevent the blood sample retained in the bore from exiting the bore when the blood collection device is subsequently transported.

As stated above, the aspirator assembly used with aspirator system can be similar to that described in U.S. application Ser. No. 07/935,907. The aspirator assembly comprises a casing including sleeves and an extension having an opening therein. Tubes are attached to the sleeves and one of the tubes is further coupled to a standard surgical needle or the like which is inverted into the patient to provide communication with the patient's vascular system. Alternately, a plug can be inserted into one of the cylindrical sleeves to block this sleeve.

A plug is inserted into the opening of the extension to prevent blood from escaping through this opening the aspirator assembly. The plug is comprised of a resilient material and has a perforation therein to allow insertion of the blunt cannula. When the cannula is absent from the perforation, the perforation is tightly closed to prevent leakage of fluid from the aspirator assembly.

The contour of the cannula tip and the tightness of the seal of the plug perforation are correlated. This correlation assures that the force needed to pass the blunt cannula tip into the perforation of the plug is considerably less than the force required to cause the tip of the blunt cannula to penetrate normal human skin. The perforation in the plug preferably allows the blunt cannula to initial penetration into the plug with a relatively small amount of force. The initial insertion of the blunt cannula holds the blunt cannula in alignment for further application of force to move the cannula tip into the aspirator assembly.

When the cannula is inserted into the aspirator assembly through the plug, the cannula extends into the portion of the aspirator assembly that communicates with the vascular system of the patient. Therefore, blood passes into the bore of the cannula and further into the small blood collection chamber of the blood collection device. In an alternative embodiment, the bore of the cannula acts as the collection chamber.

Additional objects and advantages of the invention will be set forth in the description which follows, and in part will from the description, or may be learned by practice of the invention. The objects and advantages of the invention may be realized by means of the instrumentalities and combinations particularly pointed out in the appended claims.

DETAILED DESCRIPTION OF THE PREFERRED EMBODIMENTS

Figure 1:
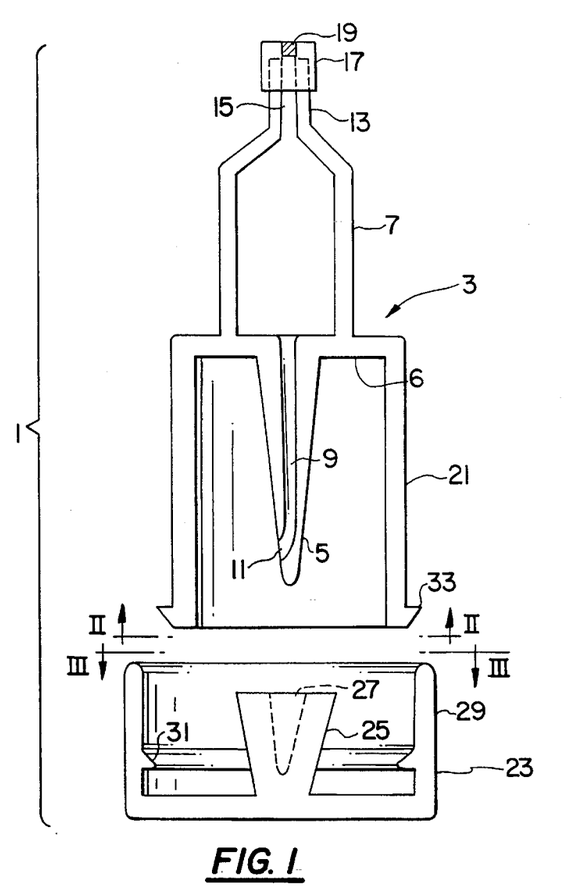
FIG. 1 is a side view of an embodiment of the vented fluid collection device of the present invention.

FIG. 1 illustrates a vented blood collection apparatus 1 in accordance with the present invention. The vented blood collection apparatus includes a blood collection device 3 having a blunt cannula 5 and small blood collection chamber 7. The blunt cannula 5 has a bore 9 therein which communicates with the small blood collection chamber. The chamber 7 has a volume of about 2 cubic centimeters (2 ml) or less. The bore 9 opens distally at 11. In the illustrated embodiment, the opening 11 is through the side wall of the blunt cannula 5.

Figure 16:
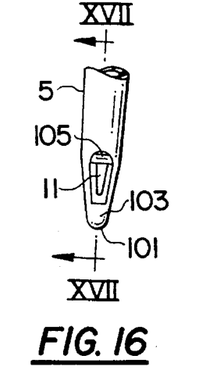
FIG. 16 illustrates an embodiment of the cannula of the fluid collection device of the present invention.
Figure 17:
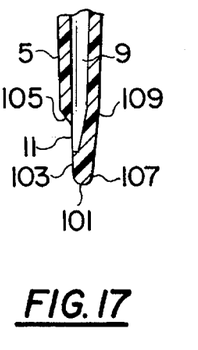
FIG. 17 is a cross sectional view of the cannula taken along lines XVII—XVII in FIG. 16.

Examples of the blunt cannula 5 of the present invention are shown in FIGS. 16–20. Referring to FIGS. 16 and 17, cannula 5 has a rounded tip 101 and a recessed side 103. The radius of curvature of tip 101 is about 0.25 mm.

Bore 9 tapers from a larger diameter proximally to a smaller diameter distally. Near the distal end of cannula 5, bore 9 is inclined at an angle of approximately 20° toward the side 103 and has an opening 11 through side 103. Cannula 5 has a smooth slanted edge 105 immediately proximal to opening 11.

In the embodiment illustrated in FIGS. 16–17, beyond the rounded tip 101, as the cannula 5 extends proximally, it flares out into a conical section 107 having an angle of about 30°, as shown on the right side of FIG. 17. Thence, the cannula 5 extends into a conical section 109 having a smaller angle than 30°, such as an angle of about 20°, also as shown on the right of FIG. 17.

Figure 18:
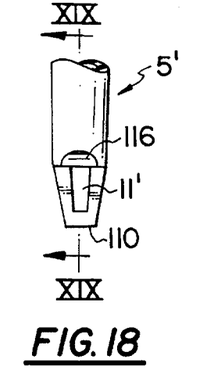
FIG. 18 is an alternate embodiment of the cannula of the fluid collection device of the present invention.
Figure 19:
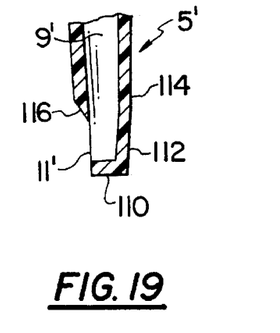
FIG. 19 is a cross sectional view of the cannula taken along lines XIX—XIX in FIG. 18.

FIGS. 18 and 19 show a cannula 5' in accordance with the invention having a modified tip. The end 110 of cannula 5' is essentially flat and has a diameter of about 1.0 mm. The tip angle at 112 is about 15° and extends proximally into a section 114 having a smaller angle of about 10°, as seen on the right hand side of FIG. 19. The flat end surface 110 has an area of about 0.78 square mm which is of circular shape. One side of the distal end of cannula 5' is recessed at 116 and has an opening 11' extending therethrough in liquid flow communication with bore 9'.

Figure 20:
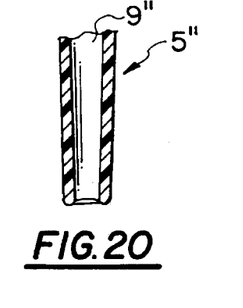
FIG. 20 is an alternate embodiment of the cannula of the fluid collection device of the present invention.

FIG. 20 shows a cannula 5" in accordance with the invention having an axial bore 9" extending therethrough and terminating with an axial opening at the distal end. The distal end of cannula 5" has a diameter of about 1.0 mm.

For both the round end and flat end blunt cannulas, the effective radius of curvature of the round end, and the diameter or surface area of the flat end, may vary as the angle of the adjacent cannula section varies from 30 degrees. Also, the effective radius of curvature may vary for plugs with silicone having different ranges of hardness to the extent that such designs allow the blunt needle tip to penetrate into the perforation at forces less than the forces required to cause the needle tip to penetrate into human skin.

As shown in the embodiment in FIG. 1, an end of the blood collection chamber 7 opposite to the blunt cannula 5 is formed as a male lab instrument connector 13, for example, to couple to a blood receiver of a lab instrument (not shown). A bore 15 extends through the male instrument connector 13 and cooperates with the blood collection chamber 7. In the illustrated embodiment, cap 17 is removably connected to the male connector 13. The cap 17 has a vent 19 which permits gas to pass therethrough but does not allow the passage of liquids, such as blood. The cap 17 is removable to allow for another instrument or device (not shown) to be connected to the male connector 13. Alternatively, the vent 19 may be formed in the bore 15 and the cap 17 may be eliminated.

Figure 2:
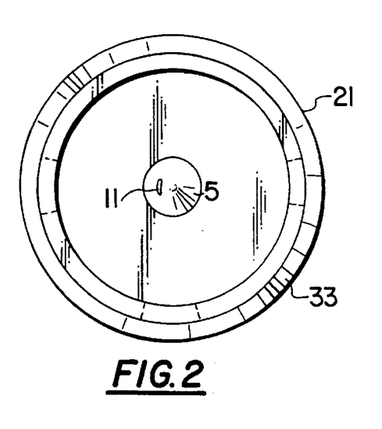
FIG. 2 is a view of the vented fluid collection device taken along lines II—II in FIG. 1.

An cannula shroud 21 extends longitudinally in the direction of the blunt cannula 5. As shown in FIG. 2, the cannula shroud 21 surrounds the blunt cannula 5 and extends beyond the distal tip of the blunt cannula 5. This protects the blunt cannula 5 from unintentional contact and acts to align the blunt cannula 5 with the perforation in the aspirator assembly to facilitate coupling of the vented blood collection apparatus 1 to the aspirator assembly 35 (see FIG. 21). Also, the cannula shroud 21 prevents the tip of the blunt cannula 5 from being inserted too deeply into the aspirator assembly 35 to prevent the blunt cannula 5 from being damaged by contacting the opposing wall of chamber 48 of the aspirator assembly.

Figure 21:
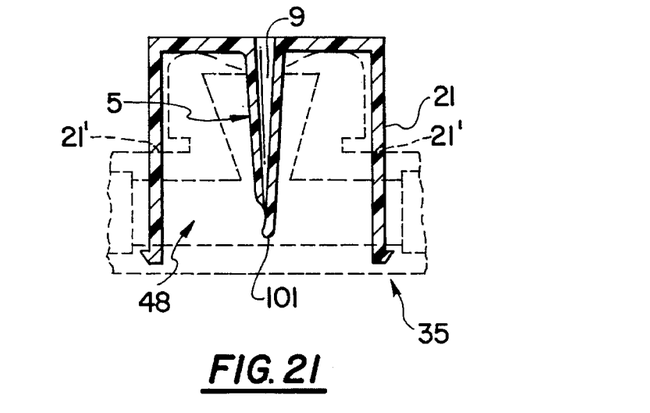
FIG. 21 illustrates insertion of the blunt cannula into the aspirator assembly.

In the illustrated embodiment, cannula shroud 21 is cylindrical. However, the shape of the cannula shroud is not limited to that shown in this embodiment. Furthermore, as may be necessary to accommodate the aspirator assembly, cutouts may be defined on diametrically opposite sides of the shroud to a height 21' as shown in FIG. 21.

Figure 3:
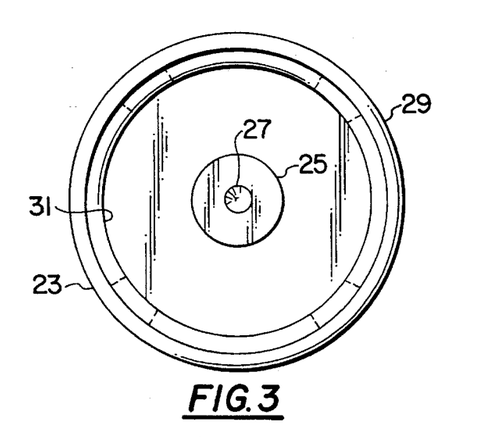
FIG. 3 is a view of the cannula cap of the vented fluid collection device taken along lines III—III in FIG. 1.
Figure 4:
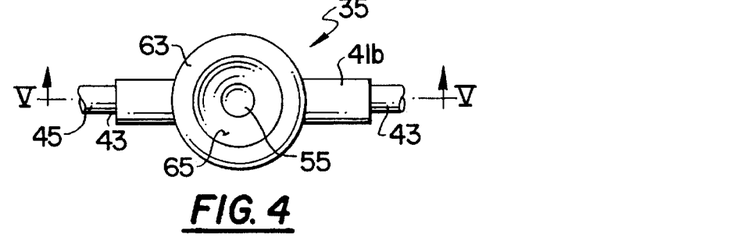
FIG. 4 is a top view of an aspirator assembly which may be used with the vented fluid collection device.

The vented blood collection device 1 as shown in FIG. 1 further comprises a cannula cap 23. The cannula cap 23 comprises a cannula cover 25 having a cannula tip receiving recess 27. When cannula 5 is fully advanced into recess 27, the cannula cover 25 seals bore 11. The cannula cap 23 further comprises a wall 29 which is shaped to cooperate with the cannula shroud 21. Accordingly, in the illustrated embodiment, the wall 29 is cylindrical as shown in FIG. 3.

The cannula cap 23 further comprises a locking flange 31 that extends inward from the circumferential wall 29 toward the cannula cover 25. This flange 31 engages the shroud flange 33, which extends outwardly from the cannula shroud 21 (see FIG. 1), to secure the cannula cap 23 to the cannula shroud 21.

In the preferred embodiment, once engaged, cannula cap 23 is permanently locked above flange 33; however, partial displacement of cap 23 between cannula 5 and flange 33 is possible to allow venting of bore 11 through recess 27. Both flanges 31 and 33 and/or shroud 21 and wall 29 may be deformable to facilitate repeated engagement and disengagement. Alternatively, as shown by the phantom lines in FIGS. 2 and 3, the flanges 31 and 33 may be sectional to provide ease in engagement.

FIGS. 4–9 show an aspirator assembly 35 with which the blunt cannula vented blood collection apparatus of the invention may be used. Assembly 35 comprises a housing 37 having a casing 39. Casing 39 has cylindrical sleeves 41a and 41b which receive tube ends 43 of tubes 45. One of the tubes 45 is further coupled to a standard surgical needle (not shown) or the like which is inserted into the patient to provide communication with the patient's vascular system. Alternately, a plug (not shown) may be inserted into one of the cylindrical sleeves 41a or 41b to block this sleeve.

Figure 9:
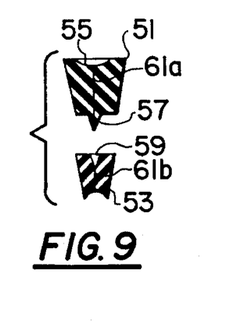
FIG. 9 shows the cooperation between the first and second sections of the plug of FIG. 7.
Figure 10:
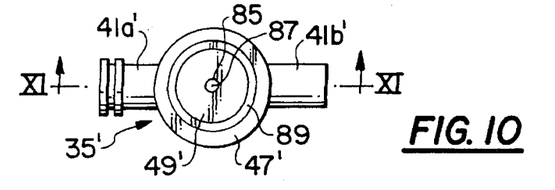
FIG. 10 is a top view of an alternate aspirator assembly used with the vented fluid collection device.

Casing 39 has an upright externally threaded extension 47 with an elliptical frustum-shaped bore that communicates with chamber 48 of the aspirator assembly 45 and is filled with a plug 49. Plug 49 comprises an upper part 51 and a lower part 53. As shown in FIG. 9, the top of upper part 51 has an arcuate recess 55, while the bottom has a projecting ridge 57.

Figure 5:
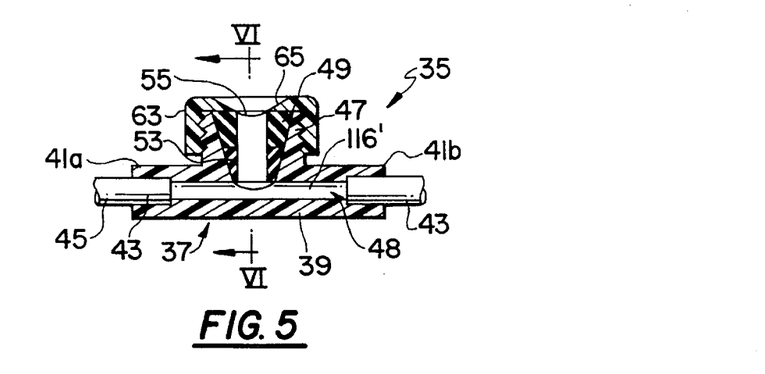
FIG. 5 is a view of the aspirator assembly taken along lines V—V in FIG. 4.
Figure 6:
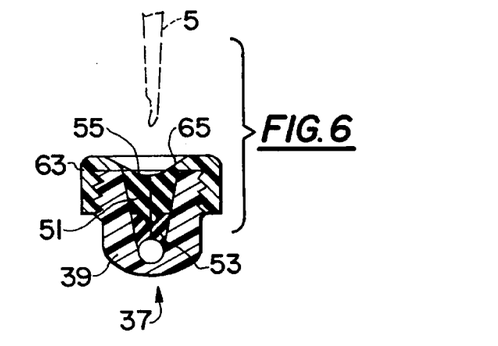
FIG. 6 is cross-sectional view of the aspirator assembly as shown taken along lines VI—VI in FIG. 5.
Figure 7:
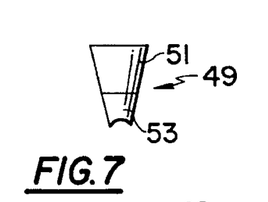
FIG. 7 is a view of the two-section plug of the aspirator assembly of FIG. 4.
Figure 8:
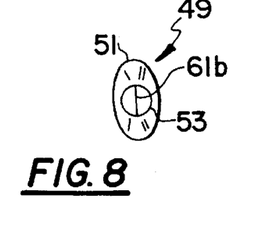
FIG. 8 is a view of the plug as shown taken along lines VIII—VIII in FIG. 7.

Bottom plug 53 has an upper recess 59 shaped to snugly receive the ridge 57. The bottom surface of plug part 51 is held to the top of plug part 53, so that the two fit together, as seen in FIGS. 5 and 6, when they are within the extension 47. A perforation 61a extends through plug part 51 from the top recess 55 through the bottom ridge 57. The perforation 61a is in longitudinal alignment with the sleeves 41 of casing 39. Lower plug part 53 likewise has a perforation 61b aligned with perforation 61a, to form a continuous perforation through the plug 49.

Upper plug part 51 is made of a more complaint material than lower part 53, although both materials can be made of silicone rubber, for example, or the like. Cap 63 fits on extension 47 as heretofore described. The cap bore 65 has its bottom opening aligned with perforation 61a.

FIGS. 10–15 show an aspirator assembly 35' in accordance with the invention which has a resilient plug having an orifice or perforation extending therethrough, and a different flow path than that of aspirator assembly 35. Aspirator assembly 35' has a modified housing 37' with a modified casing 39'. Casing 39' has cylindrical sleeves 41a' and 41b' which receive tube ends 43 (see FIG. 5).

Figure 12:
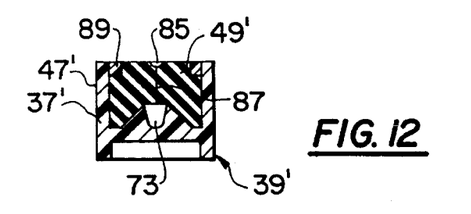
FIG. 12 is a cross sectional view of the alternate aspirator assembly taken along lines XII—XII in FIG. 11.
Figure 13:
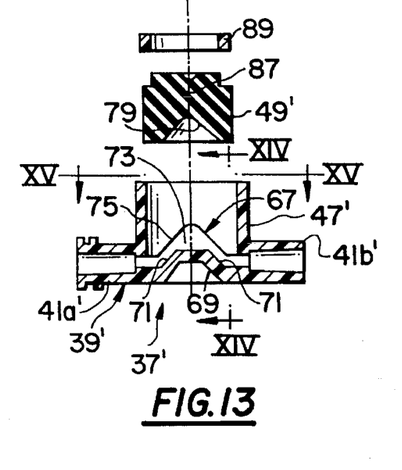
FIG. 13 illustrates the cooperation of the components of the alternate aspirator assembly of FIG. 11.
Figure 14:
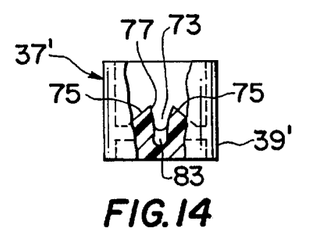
FIG. 14 is a cross sectional view taken along lines XIV—XIV in FIG. 13.

The casing 39' has a modified chamber 48'. The lower part of casing 39' has a raised hump 67 having a raised floor 69 with slanted sides 71. A hollow 73 extends longitudinally through hump 67, as shown in FIG. 12, to divide the hump into two opposing ridges 75.

Figure 11:
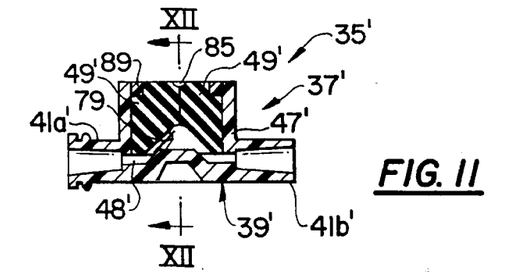
FIG. 11 is a view of the alternate aspirator assembly taken along lines XI—XI in FIG. 10.
Figure 15:
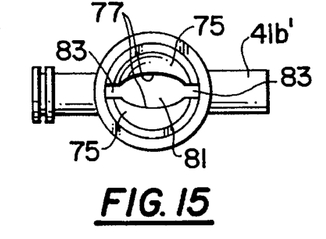
FIG. 15 is a top view of the alternate aspirator assembly taken along lines XV—XV in FIG. 13.

As seen in FIGS. 11 and 15, the upper side edges 77 of the ridges 75 are curved upwardly and outwardly. The plug or septum 49' has a lower conical recess 79. Recess 79 is shaped to conform to the shape of ridges 75, so that a conduit is provided by the hollow 71 and the part of plug recess 79 extending about hollow 71. Because of the aforementioned curvature of the ridges 75, the conduit has an enlarged central portion 81 and two smaller portions 83 in flow connection therewith.

The upper surface of plug 49' has a small central target recess 85 of a generally conical or arcuate shape. An orifice or perforation 87 extends through the axis of plug 49' to connect the center of the upper recess 85 to the center of lower plug recess 79. This perforation in a preferred embodiment is made by penetrating the plug 49' with a steel needle having an outside diameter of 1.5 mm, however, this perforation can be made by other means as chosen by the artisan.

The annular upper perimeter of plug 49' is recessed to receive an annular plastic retainer ring 89. Ring 89 can be held against the inner wall of extension 47' as by adhesive, to thus retain plug 49' therein.

The chamber 48' is enlarged to accommodate the blunt needle. As a result, flow velocity from either of the more narrow conduit flow paths 83 into the larger central conduit portion 81 is reduced. The raised floor 69 and its slanted sides 71 create a turbulent flow path for liquid passing therethrough. This turbulence increases the probability of the flowing liquid catching air bubbles which adhere to the walls of chamber 48' and shearing the bubbles away from the walls during initial preparation of the assembly before attachment to the patient. Thus, the air bubbles are removed to avoid a possible embolism or other injury caused by injection of an air bubble into the vasculature of the patient during subsequent use of the assembly.

The aspirator assemblies 35 and 35' are of particular use when the aspirating means is the blunt cannula shown in FIGS. 1 and 16–19. With respect to assembly 35, the blunt cannula 5 may be inserted through the cap bore 65 into the top recess 55 of upper plug part 51. The arcuate shape of the recess 55 helps to guide the cannula 5 toward the perforation 61a. Further downward pressure on cannula 5 moves it easily through perforation 61a, through lower ridge 57. As the cannula 5 enters the top of lower plug part 53, the angled recess 59 helps to guide cannula 5 through the lower perforation 61b. The cannula 5 then passes completely through lower plug perforation 61b into the bore chamber 48, as shown in FIG. 21.

In this FIG. 21 position, it can be seen that the arrangement of cannula shroud 21 prevents tip 284 from striking the opposing wall of chamber 48. Blood is then aspirated through opening 11 and bore 9 of the cannula 5 and is collected in the blood collection chamber 7. The patient's systemic blood pressure causes the blood to flow through the bore 9 of the cannula 5 and into the blood collection chamber 7. Alternatively, an external lab device (not shown) may be removably attached to the instrument connector 13 to provide additional pressure to aid in siphoning the blood into the bore 9 and blood collection chamber 7. Next, the cannula 5 is withdrawn from perforations 61b and 61a, and the blood in blood collection chamber 7 can be taken elsewhere.

The embodiment of the plug 49' of FIGS. 10–15 has dimensions of height of about 0.5 inches (12.7 mm) from the upper surface of the plug 49' extending about recess 85, to the lower surface extending about lower plug recess 79. The diameter of the plug 49' through its largest dimension is about 0.545 inches (13.84 mm). The angle of the recess 79 is about 45°, and the diameter of the recess 79 at its bottom are about 0.40 inches (10.16 mm) and the depth of the recess 79 is about 0.175 inches (4.44 mm).

The recess of the plug 49' to receive the retainer ring 89 is about 0.10 inches (4.54 mm) deep and 0.75 inches (1.9 mm) wide. The upper diameter of the recess 85 has a depth of about 0.025 inches (0.63 mm) and a width of about 0.125 inches (3.18 mm).

The silicone rubber for the plugs 49' may be 50 to 60 Durometer-A medical grade.

With the plug 49' design of FIGS. 10–15, with a silicone having a hardness of about 50 to 55 Durometer-A medical grade, the depth of penetration into the plug with the blunt cannula 5 made of polycarbonate or the like with the force of one pound applied perpendicular to the plug 136" surface is 0.2 inches (5 mm). With a force of 2 pounds (889,600 dynes), the blunt cannula 5 will penetrate the plug 0.25 inches (6.35 mm).

In contrast, using the same blunt cannula 5 penetration of intact normal human skin of the dorsum of the hand does not occur at a force of 2 pounds (889,600 dynes). In further contrast, a sharp 20-gauge steel needle of the type conventionally used with the prior art results in the penetration of the skin of the dorsum of the hand with a force of about 0.12 pounds (53,376 dynes).

Since the force required to pass the tip of the blunt cannula 5 into the plug or septum is considerably less than the force required to penetrate the surface of normal intact human skin of the hand, accidental misdirection of such forces through the blunt needle tip against the skin will not result in penetration. Therefore, the risk of needle stick while obtaining a blood sample through the septum with the blunt needle should be virtually eliminated.

The channeling of the movement of the cannula 5 through the remainder of plug 49' is effected by the perforation 87 guiding the cannula 5 in the proper direction. Once the initial penetration of cannula 5 occurs, there is little likelihood of misdirection of the blunt cannula 5.

With the plug 49' of the described design for FIGS. 10–15, total penetration of the plug 49' by a polycarbonate cannula 5 having dimensions heretofore described to position the tip 101 within aspirator chamber 48', as illustrated in FIG. 21 for aspirator chamber 48', is performed by a force of about 4.2 pounds (18,681,600 dynes) applied perpendicular to the plug surface.

Cannula 5 having tips 101 with a radius of curvature of 0.20 mm to about 1 mm may also be used with the plug 49' with dimensions previously described. With larger plug 49', blunt needle tips having larger radius of curvature than 1 mm, may be used, such as a radius of 2.5 mm.

With regard to the easy penetration of the skin achieved by the typical steel needle, the cannula 5' with end 110 of FIG. 18 and 19 fails to penetrate the skin of the dorsum of the hand when directed against it at a force of 2.3 pounds (1,023,040 dynes). Hence, it too is much less likely than the conventional steel needle to penetrate the human skin accidentally when the cannula contacts the skin through casual contact.

The force required to achieve depths of penetration of 0.2 inches (5.08 mm) and 0.25 inches (6.35 mm) into the plug 49' of dimensions previously described, with the flat end cannula 5' as described for FIGS. 18 and 19, is substantially the same as the forces given for the rounded end cannula 5 of dimensions previously described. Blunt cannula 5' having a flat end 0.110 with diameters of from about 0.2 mm. to about 2 mm. may also be used with a plug 49' described previously. With plugs of larger size, cannulas 5' with flat end 110 of up to about 5 mm. diameter may be used. The cannula design of FIGS. 18 and 19 completely penetrate the previously described plug 49' into the aspirator chamber 48' at a perpendicular application force of about 5 pounds (2,224,000 dynes).

Figure 22:
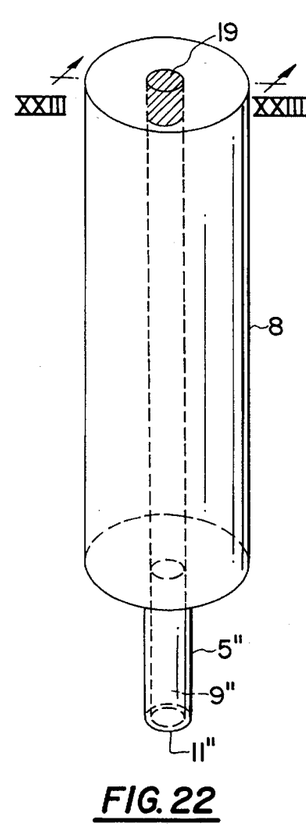
FIG. 22 is a perspective view of a second embodiment of the vented fluid collection device of the present invention having an enlarged housing and a blunt cannula wherein the bore of the blunt cannula acts as the collection chamber.

A second embodiment of the vented blood collection apparatus is shown in FIG. 22. The second embodiment comprises a blunt cannula 5" and, preferably, an enlarged housing 8 disposed about a portion of the blunt cannula 5" to facilitate handling of the blunt cannula 5". Bore 9" of blunt cannula 5" is defined axially through the blunt cannula 9".

In this embodiment, bore 9" acts as the modified blood collection chamber and has a volume of about 2 ml or less. Thus, when the bore 9" is inserted into, for example, the aspirator assembly 35 (see, for example, FIG. 6), capillary flow and/or the patient's systemic blood pressure fills bore 9" with blood.

A vented member 19 as in the first embodiment is preferably inserted in the proximal end of the bore 9" which enables gas to pass out of the bore 9" while preventing the blood sample stored therein from passing therethrough. As noted above, in most cases, no external aspiration force is needed to draw or retain the blood sample in the bore 9". However, if necessary or desirable, a lab instrument (not shown) may be removably attached to the proximal end of the blunt cannula 5" with or without the vent in place to provide an aspiration force to help draw blood out of the patient's vascular system.

Figure 23A:
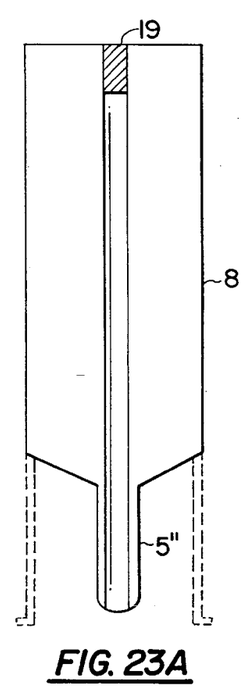
FIG. 23A is a schematic view of the second embodiment of the vented fluid collection device taken along the lines XXIII—XXIII in FIG. 22 wherein the enlarged housing is integral with the blunt cannula.
Figure 23B:
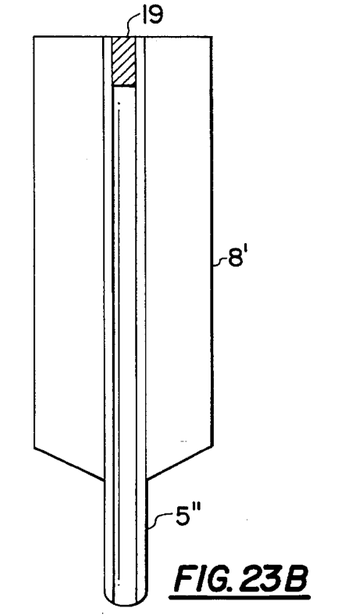
FIG. 23B is a variation of FIG. 23A wherein the blunt cannula is removably inserted into an opening in the enlarged housing.

FIG. 23A shows a schematic cross sectional view of the embodiment illustrated in FIG. 22 wherein the enlarged housing 8 is injection molded to the blunt cannula 5". Alternatively, as shown in FIG. 23B, an enlarged housing 8' can be a separate component having an opening into which the blunt cannula 5" is removably inserted.

Additional modifications of the second embodiment may be made. For example, as in the first embodiment in FIG. 1, the device of the second embodiment may further comprise a cannula shroud as shown by the phantom lines in FIG. 23A and/or cannula cap. Such a cannula shroud may be integral with or attached to the enlarged housing 8 or 8' or may be integral with or attached to the blunt cannula 5" if, for example, no enlarged housing is provided.

Figure 24:
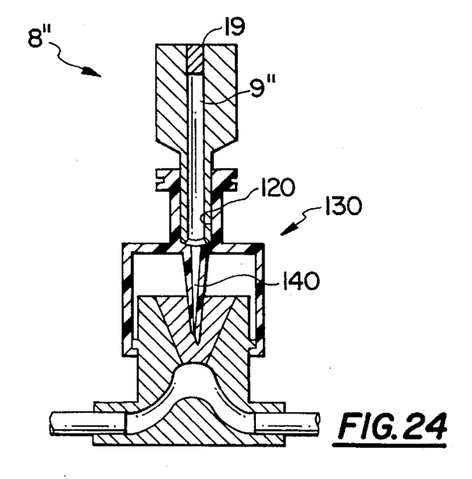
FIG. 24 is a cross sectional view of a further modification of the invention.

In a further modification, shown in FIG. 24, a truncated embodiment 8" of the blood collector is sized to be received within the bore 120 of a shrouded blunt cannula 130 having a distal bore 140. Heparin may be included within bore 140 or bore 9". In operation, after blood has been received through blunt cannula 130 into bore 9'", the blood collector 8" is separated from the shrouded blunt cannula 130 and cannula 5'" is capped for transport to the lab.

Exemplary preferred embodiments of the invention are described above in relation to a blood collection system. However, other embodiments of the invention exist wherein the above system is used for collection of other types of body fluids.

Although the preferred embodiments of this invention has been described, it will be apparent to those skilled in the art that various changes and modifications may be made therein without departing from the invention. Therefore, the claims are intended to include all such changes and modifications that fall within the true spirit and scope of the invention.

What is claimed is:

1. An extra-corporeal fluid collection system, comprising:
   a blunt cannula having a proximal end, a distal end and a bore defined therethrough;
   wall means defining a collection chamber in communication with the bore for collecting a fluid sample which passes through said bore, said collection chamber having a volume of about 2 ml or less;
   means defining an opening in said collection chamber wall; means for providing communication between said collection chamber and outside atmosphere;
   vent means for allowing gas to pass through said opening and for preventing said fluid sample collected in said collection chamber from passing through said opening; and
   a cap for selectively covering said opening, said vent means being provided in said cap.

2. An extra-corporeal fluid collection system as claimed in claim 1, wherein said bore opens distally at a point proximal to a distal most tip of said blunt cannula.

3. An extra-corporeal fluid collection system as claimed in claim 1, further comprising:
   a cannula shroud coaxially surrounding said blunt cannula and extending distally beyond said distal end of said blunt cannula; and
   a cannula cap;
   said cannula shroud and said cannula cap including complementary coupling means for selectively engaging to couple said cannula cap to said cannula shroud to enclose said blunt cannula.

4. An extra-corporeal fluid collection system as claimed in claim 1, further comprising:
   a device having a flow channel adapted for communication through a catheter with one of an organ and body lumen of a mammal having a fluid to be sampled therein;
   said blunt cannula being adaptable to be coupled to said device to communicate said bore with said flow channel to allow said fluid sample to flow through said bore into said collection chamber.

5. An extra-corporeal fluid collection system as claimed in claim 4, said device having an aspiration opening therein in communication with said flow channel, said aspiration opening having a plug therein for preventing fluid in said flow channel from passing through said aspiration opening when said blunt cannula is not inserted into said aspiration apparatus.

6. An extra-corporeal fluid collection system as claimed in claim 5, said plug having a perforation therein for allowing said blunt cannula to pass therethrough to communicate said bore with said flow channel.

7. An extra-corporeal fluid collection system, comprising:
   a blunt cannula having a proximal end, a distal end and a bore of substantially constant diameter defined therethrough, said bore communicating with outside atmosphere at said proximal and distal ends of said blunt cannula and collecting a fluid sample which flows into said bore at said distal end of said blunt cannula, said bore having a volume of about 2 ml or less and retaining said fluid sample therein due to frictional force between said fluid sample and an inner wall of said blunt cannula; and
   vent means for allowing gas to pass into and out of said bore and for preventing said fluid sample collected in said bore from passing out of said bore at said proximal end of said blunt cannula.

8. An extra-corporeal fluid collection system as claimed in claim 7, wherein said bore opens at a distal most tip of said blunt cannula.

9. An extra-corporeal fluid collection system as claimed in claim 7, further comprising a housing having an opening therethrough, said blunt cannula removably inserting into said opening such that said distal end of said blunt cannula extends from said opening.

10. An extra-corporeal fluid collection system as claimed in claim 7, further comprising a housing integral with and disposed about said blunt cannula such that said distal end extends from said housing.

11
11. An extra-corporeal fluid collection system as claimed in claim 7, further comprising:

a device having a flow channel adapted for communication through a catheter with one of an organ and body lumen of a mammal having a fluid to be sampled therein;

said blunt cannula being adaptable to be coupled to said device to communicate said bore with said flow channel to allow said fluid sample to pass into said bore.

12. An extra-corporeal fluid collection system as claimed in claim 11, said device having an aspiration opening therein in communication with said flow channel, said aspiration opening having a plug therein for preventing fluid in said flow channel from passing through said aspiration opening when said blunt cannula is not inserted into said aspiration apparatus.

13. An extra-corporeal fluid collection system as claimed in claim 12, said plug having a perforation therein for allowing said blunt cannula to pass therethrough to communicate said bore with said flow channel.

14. A method for using an extra-corporeal fluid collection system to collect a fluid sample, comprising the steps of:

providing a blunt cannula having a proximal end, a distal end and a bore of substantially constant diameter defined therethrough, said bore communicating with outside atmosphere at said proximal and distal ends of said blunt cannula, said bore having a volume of about 2 ml or less, the blunt cannula having vent means for allowing gas to pass into and out of said bore and for preventing said fluid sample collected in said bore from passing out of said bore at said proximal end of said blunt cannula;

inserting the distal end of the blunt cannula into a device having a flow channel adapted for communication through a catheter with one of an organ and body lumen of a mammal having a fluid to be sampled therein, to enable a sample of said fluid to pass into said bore;

allowing gas contained in said bore to pass out of said bore through said vent when said sample of said fluid passes into said bore; and retaining said fluid sample in said bore while allowing communication between said fluid sample and an atmosphere outside said bore.

15. A method as claimed in claim 14, further comprising the step of allowing systemic blood pressure of said mammal to pump said fluid sample into said bore when said flow channel communicates with said body lumen.

16. An extra-corporeal fluid collection system, comprising:

a blunt cannula having a proximal end, a distal end and a bore defined therethrough;

wall means defining a collection chamber in communication with the bore for collecting a fluid sample which passes through said bore, said collection chamber having a volume of about 2 ml or less;

means defining an opening in said collection chamber wall means for providing communication between said collection chamber and outside atmosphere;

12 vent means for allowing gas to pass through said opening and for preventing said fluid sample collected in said collection chamber from passing through said opening;

a cannula shroud coaxially surrounding said blunt cannula and extending distally beyond said distal end of said blunt cannula; and a cannula cap;

said cannula shroud and said cannula cap including complementary coupling means for selectively engaging to couple said cannula cap to said cannula shroud to enclose said blunt cannula.

17. An extra-corporeal fluid collection system as claimed in claim 16, wherein said bore opens distally at a point proximal to a distal most tip of said blunt cannula.

18. A method for using an extra-corporeal fluid collection system to collect a fluid sample, comprising the steps of:

providing an extra-corporeal fluid collection system including:

a blunt cannula having a proximal end, a distal end and a bore defined therethrough;

wall means defining a collection chamber in communication with the bore for collecting a fluid sample which passes through said bore, said collection chamber having a volume of about 2 ml or less;

means defining an opening in said collection chamber wall means for providing communication between said collection chamber and outside atmosphere;

vent means for allowing gas to pass through said opening and for preventing said fluid sample collected in said collection chamber from passing through said opening;

a cannula shroud coaxially surrounding said blunt cannula and extending distally beyond said distal end of said blunt cannula; and a cannula cap;

said cannula shroud and said cannula cap including complementary coupling means for selectively engaging to couple said cannula cap to said cannula shroud to enclose said blunt cannula;

inserting the distal end of the blunt cannula into a device having a flow channel adapted for communication through a catheter with one of an organ and body lumen of a mammal having a fluid to be sampled therein, to enable a sample of said fluid to pass into and through said bore and into said collection chamber;

allowing gas contained in said bore and collection chamber to pass out through said vent when said sample of said fluid passes into said chamber;

retaining said fluid sample in said collection chamber; and coupling said cap to said shroud.

19. A method as claimed in claim 18, further comprising the step of allowing systemic blood pressure of said mammal to pump said fluid sample through said bore into said collection chamber when said flow channel communicates with said body lumen.

* * * * *